(12) United States Patent
Hui et al.

(10) Patent No.: US 9,392,967 B2
(45) Date of Patent: Jul. 19, 2016

(54) USER INTERFACE AND METHOD TO DISCOVER HEARING SENSITIVITY OF USER ON SMART PHONE

(71) Applicant: BITwave Pte Ltd, Singapore (SG)

(72) Inventors: Siew Kok Hui, Singapore (SG); Eng Sui Tan, Singapore (SG)

(73) Assignee: BITWAVE PTE LTD., Singapore (SG)

( * ) Notice: Subject to any disclaimer, the term of this patent is extended or adjusted under 35 U.S.C. 154(b) by 243 days.

(21) Appl. No.: 14/056,369

(22) Filed: Oct. 17, 2013

(65) Prior Publication Data

US 2014/0142463 A1    May 22, 2014

Related U.S. Application Data

(60) Provisional application No. 61/728,777, filed on Nov. 20, 2012.

(51) Int. Cl.
*A61B 5/12* (2006.01)
*A61B 5/00* (2006.01)

(52) U.S. Cl.
CPC ............... *A61B 5/123* (2013.01); *A61B 5/6898* (2013.01); *A61B 5/742* (2013.01)

(58) Field of Classification Search
CPC .......... A61B 5/12; A61B 5/121; A61B 5/123; A61B 5/125
See application file for complete search history.

(56) References Cited

U.S. PATENT DOCUMENTS

| 3,970,785 A * | 7/1976 | Meyer ..................... A61B 5/121 73/585 |
| 2007/0112279 A1 | 5/2007 | Iseberg et al. |
| 2012/0288119 A1 | 11/2012 | Apfel |

FOREIGN PATENT DOCUMENTS

| CN | 1399740 A | 2/2003 |
| WO | 03077511 A1 | 9/2003 |
| WO | 2004039126 A2 | 5/2004 |

OTHER PUBLICATIONS

Chinese Office Action dated Mar. 18, 2015 for Chinese Patent Application No. 2015031301074970, 13 pgs.
European Search Report dated Jan. 8, 2014 for European Application No. 13192433.4-1506, 6 pages.

* cited by examiner

*Primary Examiner* — Adam J Eiseman
*Assistant Examiner* — Yasmeen S Warsi
(74) *Attorney, Agent, or Firm* — Amin, Turocy & Watson, LLP

(57) ABSTRACT

Employing outputted tones on a client device and/or headset is facilitated to identify hearing sensitivity of a user for both ears at various frequency bands and provide an indication of the users hearing sensitivity as compared to a normal hearing curve of a plurality of users on the same client device and/or headset or differing client devices and/or headsets.

14 Claims, 13 Drawing Sheets

610 —

| USER 1 | | | |
|---|---|---|---|
| FREQUENCY BAND | FREQUENCY | LEFT EAR | RIGHT EAR |
| 1 | 250 | 20 | 22 |
| 2 | 500 | 26 | 31 |
| ... | | | |
| $M$ | 3500 | 63 | 52 |

620 —

| USER 2 | | | |
|---|---|---|---|
| FREQUENCY BAND | FREQUENCY | LEFT EAR | RIGHT EAR |
| 1 | 250 | 33 | 24 |
| 2 | 500 | 31 | 30 |
| ... | | | |
| $M$ | 3500 | 45 | 56 |

•
•
•

630 —

| USER $N$ | | | |
|---|---|---|---|
| FREQUENCY BAND | FREQUENCY | LEFT EAR | RIGHT EAR |
| 1 | 250 | 56 | 21 |
| 2 | 500 | 58 | 32 |
| ... | | | |
| $M$ | 3500 | 67 | 48 |

FIG. 6

USER INTERFACE AND METHOD TO DISCOVER HEARING SENSITIVITY OF USER ON SMART PHONE

CROSS REFERENCE TO RELATED APPLICATIONS

This application claims the benefit of U.S. Provisional Application Ser. No. 61/728,777 filed on Nov. 20, 2012, entitled "USER INTERFACE AND METHOD TO DISCOVER HEARING SENSITIVITY OF USER ON SMART PHONE." The entirety of this provisional application is incorporated herein by reference.

TECHNICAL FIELD

This disclosure generally relates to systems and methods that facilitate employing outputted tones on a client device and/or headset to identify hearing sensitivity of a user for both ears at various frequency bands and provide an indication of the users hearing sensitivity as compared to a normal hearing curve of a plurality of users on the same client device and/or headset or differing client devices and/or headsets.

BACKGROUND OF THE INVENTION

Many individuals suffer a certain degree of unrecognized hearing sensitivity loss that generally does no become apparent until becoming severe enough to disrupt their lives. Human hearing sensitivity degrades very slowly over a long period of time. As such, it is not easily detected by those suffering from hearing sensitivity loss. Most individuals are unaware of their hearing condition because equipment and/or facility to measure hearing sensitivity is not generally available to the public without visiting a costly hearing specialist.

Hearing sensitivity loss is not just a natural phenomenon suffered by aging people, many individuals suffer the condition due to long exposure to loud noises from the environment such as construction sites, machine rooms, combustion engines, etc. Furthermore, due to the advent of portable audio devices such as portable music players and mobile phones, many young people also suffer from severe hearing loss due to prolonged exposure to loud music from setting the volume too loud while listening through a headset.

Conventionally, specially designed equipment operated by trained hearing specialists has been employed to measure hearing sensitivity. Due to the expense, many individuals avoid having their hearing sensitivity measured until it is too late. In general, individuals who approach the specialist for help have already developed severe hearing sensitivity loss which could have been prevented in an earlier stage.

Early detection of hearing sensitivity loss can allow for measures to be taken to prevent further deterioration.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the purpose of this summary is to present some concepts related to some exemplary non-limiting embodiments in simplified form as a prelude to more detailed description of the various embodiments that follow in the disclosure.

In accordance with a non-limiting implementation, a tone is outputted corresponding to a currently selected frequency band to a currently selected ear, one or more inputs are received indicating to at least one of increase or decrease a signal level of the outputted tone, the signal level of the outputted tone is adjusted according to the one or more inputs, and a current signal level of the outputted tone for the currently selected frequency band and the currently selected ear is recorded in a hearing sensitivity testing results record.

In accordance with a non-limiting implementation, a tone generation component is configured to output a tone corresponding to a currently selected frequency band to a currently selected ear, a user interface component is configured to receive one or more inputs indicating to at least one of increase or decrease a signal level of the outputted tone and instruct the tone generation component to adjust the signal level of the outputted tone according to the one or more inputs, and a sensitivity results component is configured to record a current signal level of the outputted tone for the currently selected frequency band and the currently selected ear in a hearing sensitivity testing results record.

These and other implementations and embodiments are described in more detail below.

BRIEF DESCRIPTION OF THE DRAWINGS

FIG. 6 illustrates a diagram of exemplary non-limiting hearing sensitivity testing results records in accordance with an implementation of this disclosure.

DETAILED DESCRIPTION

Overview

Figure 1:
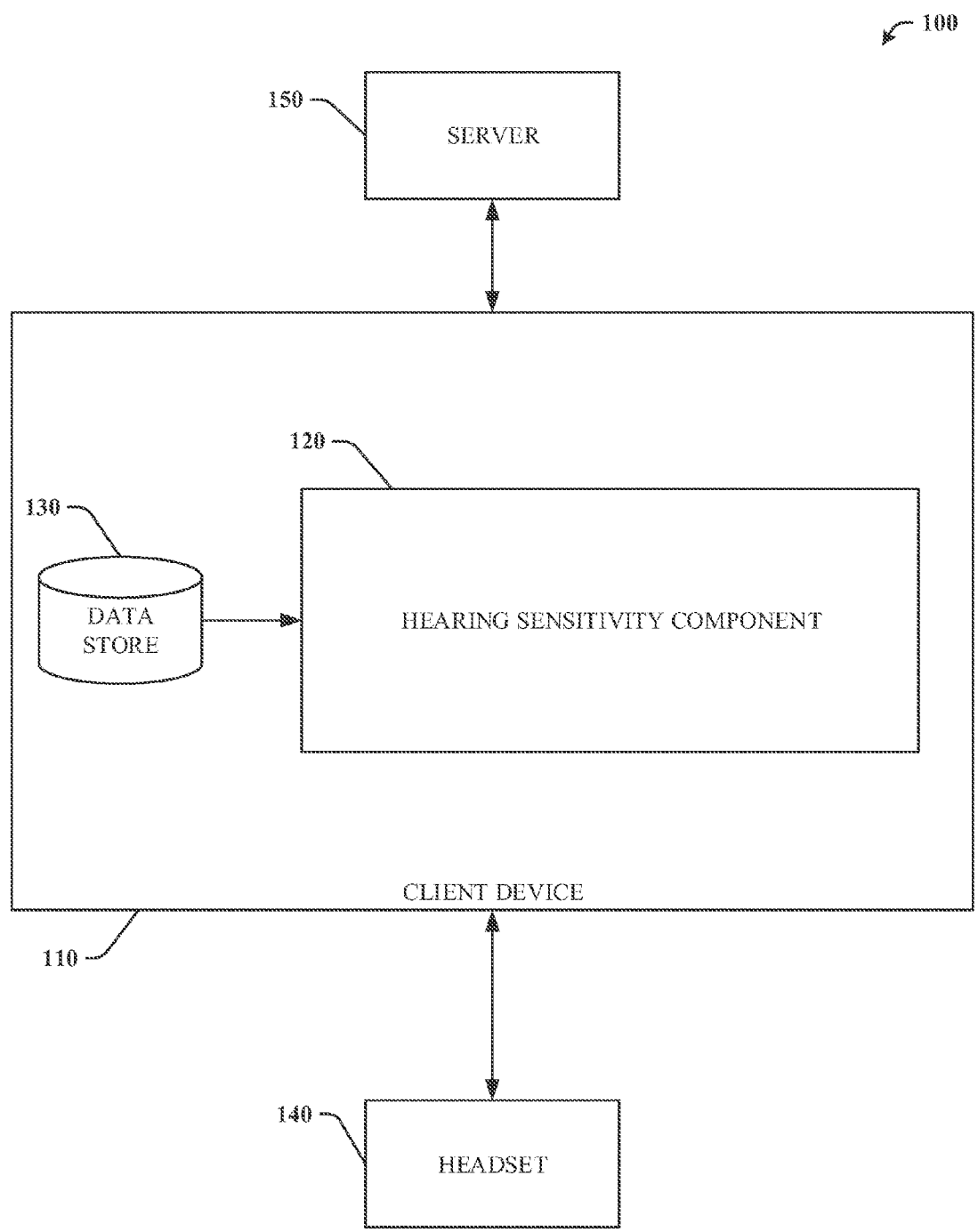
FIG. 1 illustrates a block diagram of an exemplary non-limiting system for estimating hearing sensitivity in accordance with an implementation of this disclosure.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that certain aspects of this disclosure may be practiced without these specific details, or with other methods, components, materials, etc. In other instances, well-known structures and devices are shown in block diagram form to facilitate describing this disclosure.

In situations in which systems and methods described here collect personal information about users, or may make use of personal information, the users can be provided with an opportunity to control whether programs or features collect user information (e.g., information about a user's social network, social actions or activities, profession, a user's preferences, or a user's current location), or to control whether or how to receive content from the content server that may be more relevant to the user. In addition, certain data can be treated in one or more ways before it is stored or used, so that personally identifiable information is removed. For example, a user's identity can be treated so that no personally identifiable information can be determined for the user, or a user's geographic location can be generalized where location information is obtained (e.g., such as to a city, ZIP code, or state level), so that a particular location of a user cannot be determined. The user can add, delete, or modify information about the user. Thus, the user can control how information is collected about he or she and used by a server.

In accordance with various disclosed aspects, a mechanism is provided for estimating hearing sensitivity of a user. For example, a user on a mobile device can access a hearing sensitivity component included within a client device or install the hearing sensitivity component on the client device, for example, through an application store. The hearing sensitivity component can be employed to test the user's hearing, for example using a headset, at a variety of frequency bands.

Referring now to the drawings, FIG. 1 depicts a system 100 for estimating hearing sensitivity. System 100 includes client device 110 configured to be accessed by users. Client device 110 includes hearing sensitivity component 120 that estimates hearing sensitivity of one or more users. Client device 110 can interface with server 150 to facilitate exchange of data. In addition, client device 110 can interface with headset 140 to exchange inputs and outputs, for example, with a user. Additionally, client device 110 includes a data store 130 that can store data generated or received by server 150, hearing sensitivity component 120, and headset 140 130. Data store 130 can be stored on any suitable type of storage device, non-limiting examples of which are illustrated with reference to FIGS. 11 and 12.

It is to be understood that client device 110 can concurrently interact with any suitable number of servers 150. In addition, server 150 can interact with any suitable number of client devices 110 concurrently. Moreover, while hearing sensitivity component 120 is depicted as part of client device 110, hearing sensitivity component 120 can be part of server 150 or headset 140. Furthermore, client device 110, server 150, and headset 140 can respectively receive input from users to control interaction with and presentation of content and associated information, for example, using input devices, non-limiting examples of which can be found with reference to FIG. 12.

Figure 3:
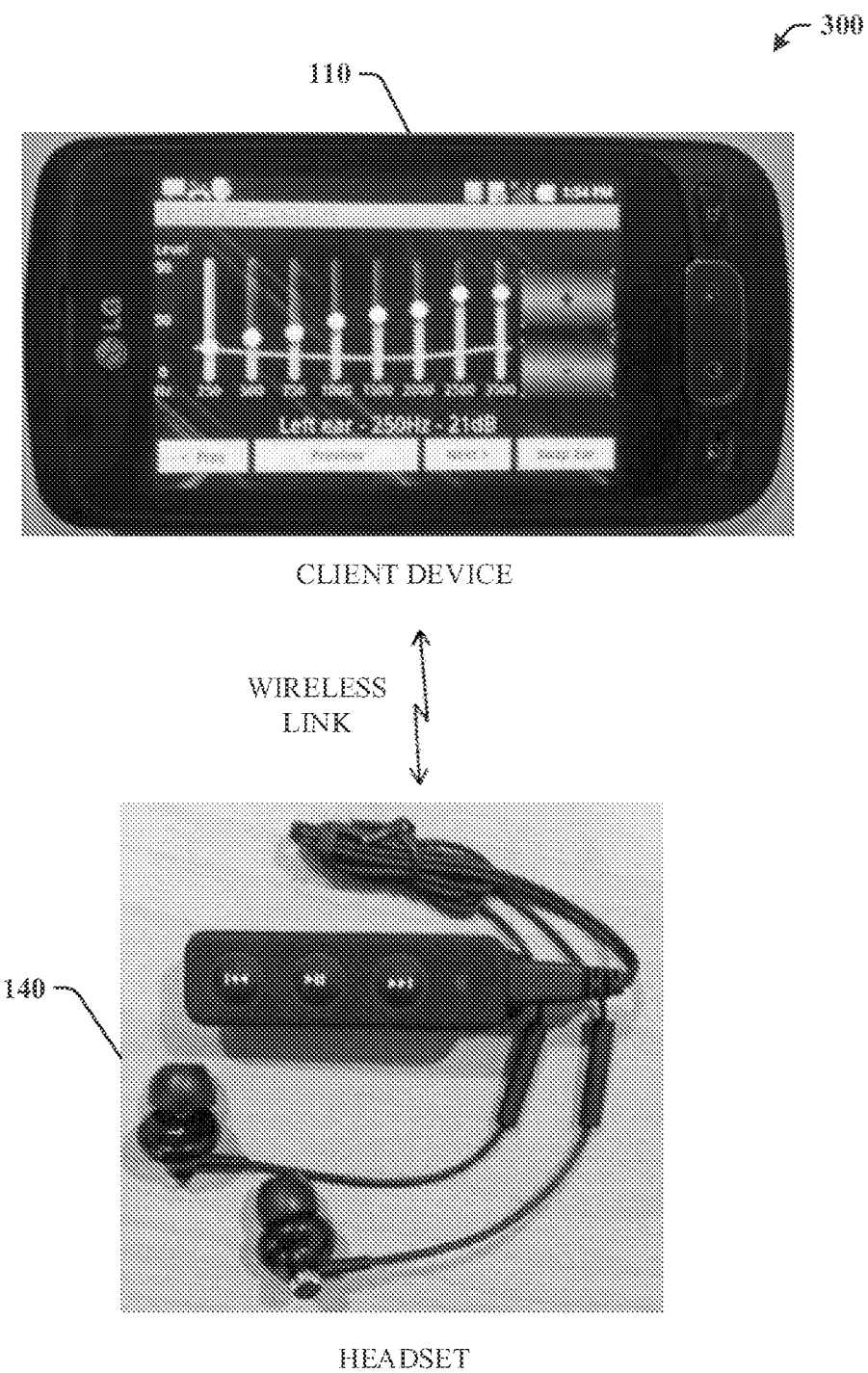
FIG. 3 illustrates a diagram of an exemplary non-limiting client device interfacing with a headset via a wireless link in accordance with an implementation of this disclosure.
Figure 4:
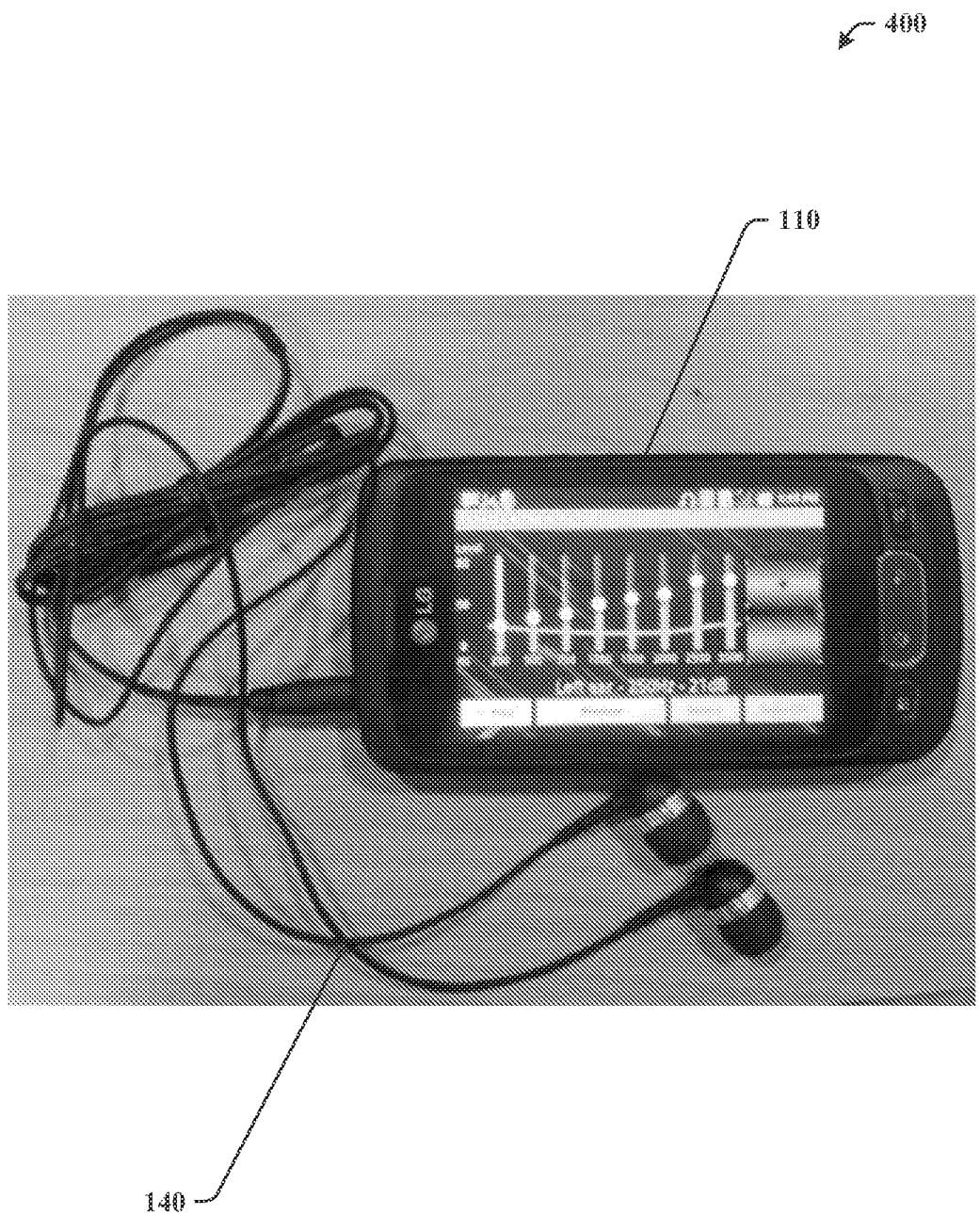
FIG. 4 illustrates a diagram of an exemplary non-limiting client device interfacing with a headset via a wired link in accordance with an implementation of this disclosure.
Figure 7:
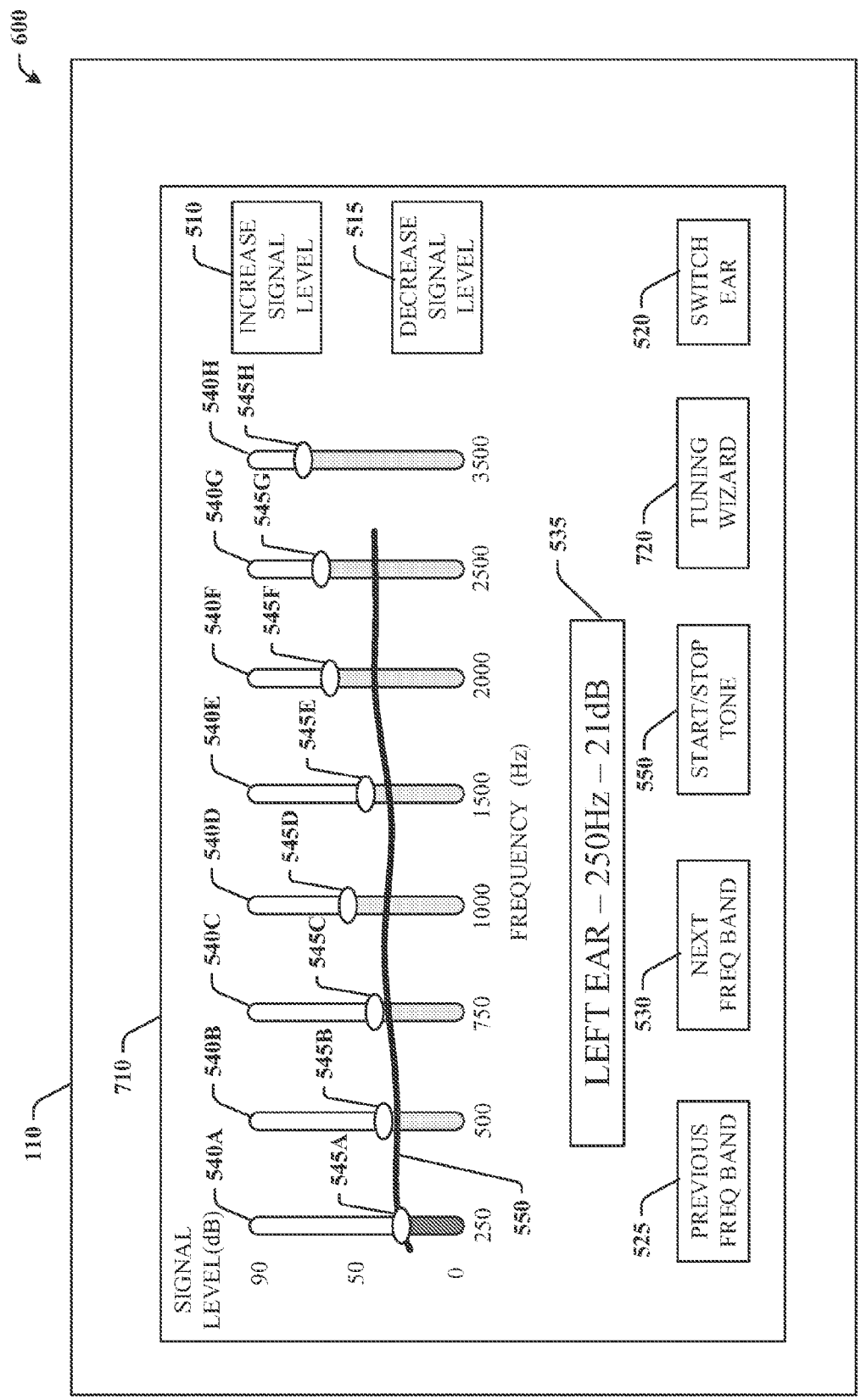
FIG. 7 illustrates a diagram of an exemplary non-limiting user interface including a tuning wizard selection element on a client device for estimating hearing sensitivity in accordance with an implementation of this disclosure.

Client device 110 and server 150, respectively include at least one memory that stores computer executable components and at least one processor that executes the computer executable components stored in the memory, a non-limiting example of which can be found with reference to FIG. 7. Furthermore, headset 140 can include at least one memory that stores computer executable components and at least one processor that executes the computer executable components stored in the memory. Client device 110 can communicate via a wired and/or wireless network with server 150. In addition, client device 110 can interface with headset 140 via wired or wireless link. For example, FIG. 3 depicts client device 110 interfacing with headset 140 via a wireless link. FIG. 4, depicts client device 110 interfacing with headset 140 via a wired link.

Client device 110 and server 150 can be any suitable type of device for recording, interacting with, receiving, accessing, or supplying data locally, or remotely over a wired or wireless communication link, non-limiting examples of include a wearable device or a non-wearable device. Wearable device can include, for example, heads-up display glasses, a monocle, eyeglasses, contact lens, sunglasses, a headset, a visor, a cap, a helmet, a mask, a headband, clothing, camera, video camera, or any other suitable device capable of recording content that can be worn by a human or non-human user. Non-wearable device can include, for example, a mobile device, a mobile phone, a camera, a camcorder, a video camera, personal data assistant, laptop computer, tablet computer, desktop computer, server system, cable set top box, satellite set top box, cable modem, television set, monitor, media extender device, blu-ray device, DVD (digital versatile disc or digital video disc) device, compact disc device, video game system, portable video game console, audio/video receiver, radio device, portable music player, navigation system, car stereo, motion sensor, infrared sensor, or any other suitable device capable of recording content. Moreover, client device 110 and server 150 can include a user interface (e.g., a web browser or application), that can receive and present displays and data generated locally or remotely.

Figure 2:
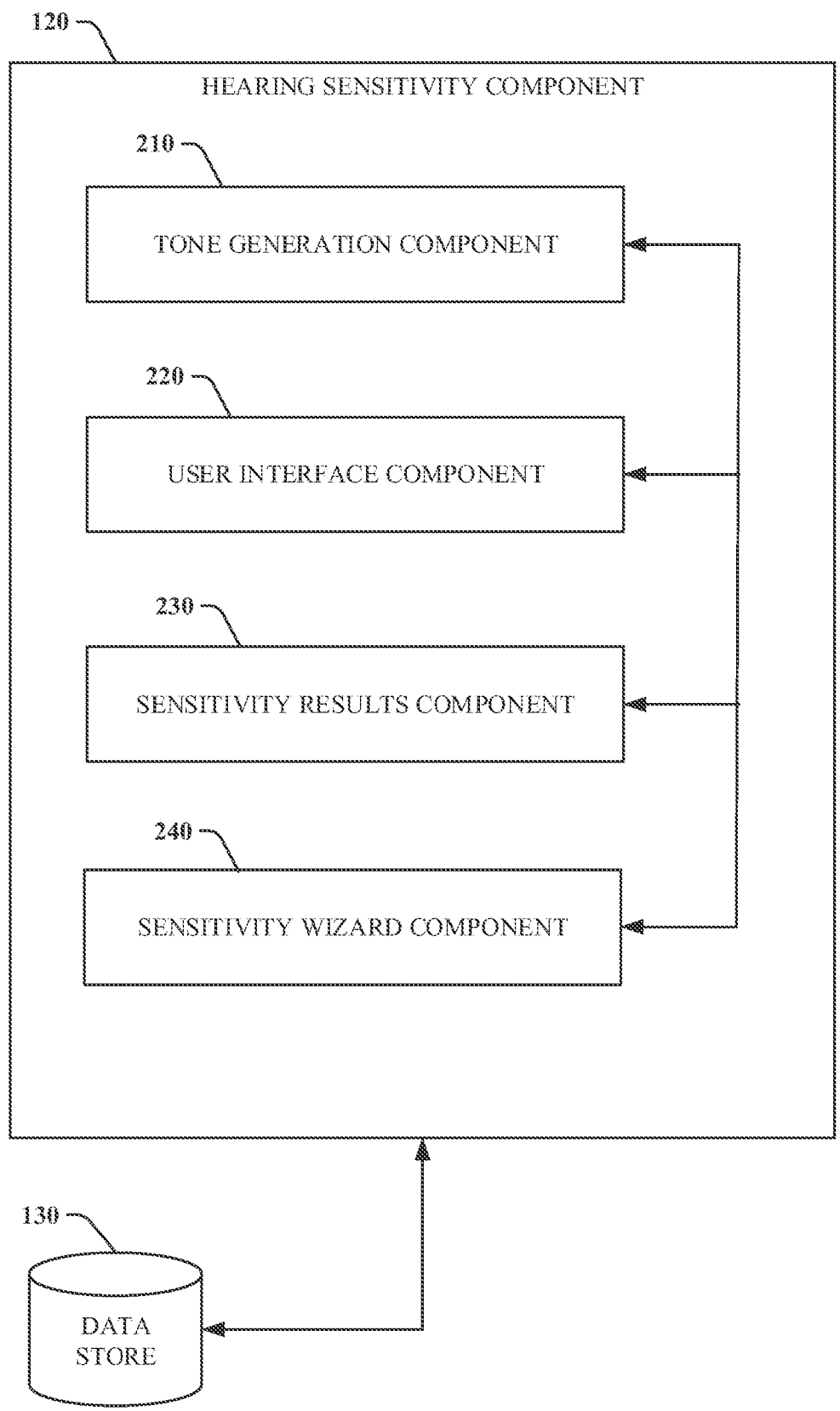
FIG. 2 illustrates a block diagram of an exemplary non-limiting hearing sensitivity component that estimates hearing sensitivity of one or more users in accordance with an implementation of this disclosure.

FIG. 2 illustrates hearing sensitivity component 120 that estimates hearing sensitivity of one or more users. Hearing sensitivity component 120 includes tone generation component 210 that generates sine tones. For example, during hearing sensitivity testing (e.g., tuning) various sine tones can be generating corresponding to specific frequency bands for which hearing sensitivity is measured. It is to be appreciated that frequency bands depicted below are non-limiting examples of frequency bands for which hearing sensitivity can be tested, and any suitable frequency bands can be employed. Furthermore, a hertz (Hz) value identified for a frequency band below is a non-limiting representation of the frequency band which can span any specified range of frequency. For example, a frequency band of 250 Hz can span frequencies from 225-275 Hz, or 200-275 Hz, or any suitable range of frequencies. In a non-limiting example, the hertz identified for a frequency band can be a center of the frequency band. However, any suitable frequency within the frequency band can be employed to represent the frequency band. Furthermore, it is to be appreciated that frequency bands can be a uniform size or vary in size, and any suitable size(s) can be employed. For example, frequency band 500

Hz can span frequencies from 460-550 Hz and frequency band 2500 Hz can span frequencies from 2250-2750 Hz.

Hearing sensitivity component 120 also includes user interface component 220 that presents a user interface. While examples below depict a touchscreen graphical user interface, it is to be appreciated that the user interface can be audio, text, video, keyboard, mouse, microphone, eye-tracking, tactile, or any other suitable interface. For example, in an embodiment where client device 110 is a headset without a display screen, user interface can be audio and user input can be provided via voice commands through a microphone.

Figure 5:
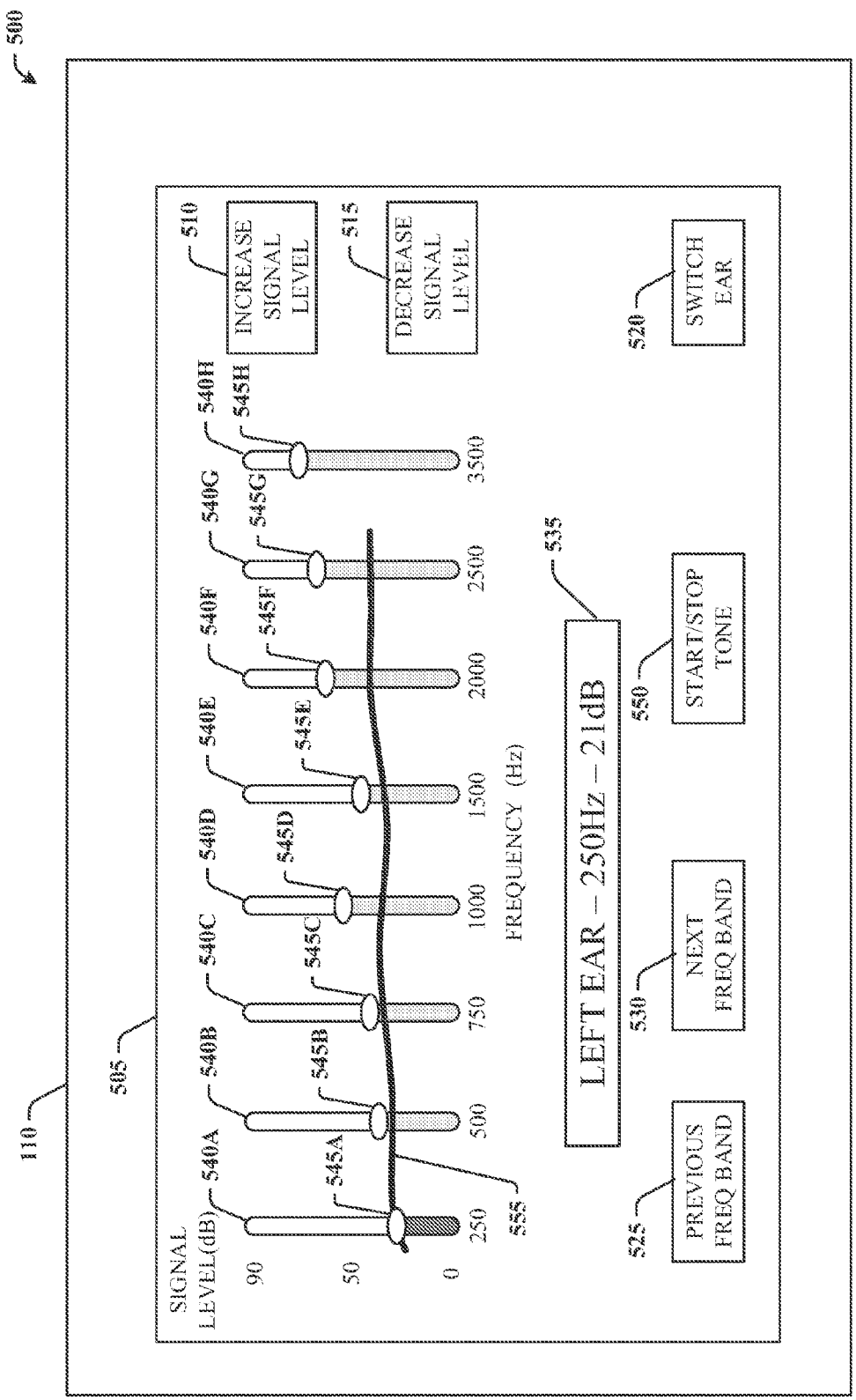
FIG. 5 illustrates a diagram of an exemplary non-limiting user interface on a client device for estimating hearing sensitivity in accordance with an implementation of this disclosure.

FIG. 5 depicts a non-limiting exemplary user interface 505 in client device 110. User interface 505 displays frequency bars 540A, 540B, 540C, 540D, 540E, 540F, 540G, and 540H corresponding to frequency bands 250 Hz, 500 Hz, 750 Hz, 1000 Hz, 1500 Hz, 2000 Hz, 2500 Hz, and 3500 Hz. It is to be appreciated that while eight frequency bars corresponding to eight frequency bands are depicted in this example, any suitable number of frequency bars corresponding to any suitable number of frequency bands can be employed. Furthermore, more frequency bars than can be displayed on the screen may be employed and user interface 505 can provide a scrolling mechanism to display frequency bars not currently visible on the display. User interface 505 also includes signal level indicators 545A, 545B, 545C, 545D, 545E, 545F, 545G, and 545H for frequency bars 540A, 540B, 540C, 540D, 540E, 540F, 540G, and 540H which indicate the signal level that the user set the corresponding frequency band during testing for the corresponding ear (e.g. left or right). In this non-limiting example, signal level is depicted in decibels (dB) from 0 to 90. However, and suitable range of decibels can be employed. Furthermore, signal level can be depicted using any suitable indicator of signal level for the frequency band, such as in a non-limiting example, absolute amplitude. User interface 505, in a non-limiting example, depicts signal level on a vertical axis and frequency on a horizontal axis. However, any suitable mechanism for depicting corresponding signal levels to frequency bands can be employed.

User interface 505 also includes increase signal level selectable element 510 that can be employed by the user to increase the signal level for a currently selected frequency band. This example depicts frequency band 250 Hz as currently selected as shown by the darker shading under signal level indicator 545A. Any suitable indication can be employed for identify the currently selected frequency band, such as in a non-limiting example, color, size, shading, patterns, outlines, shapes, highlighting, flashing, font, etc. User interface 505 also includes decrease signal level selectable element 515 that can be employed by the user to decrease the signal level for a currently selected frequency band.

User interface 505 includes previous frequency band selection element 525 that allows the user to move from a currently selected frequency band to a previous frequency band in the ordered set of frequency bands (e.g. 250 Hz, 500 Hz, 750 Hz, 1000 Hz, 1500 Hz, 2000 Hz, 2500 Hz, and 3500 Hz). For example, if the currently selected frequency band is 1000 Hz, selection of previous frequency band selection element 525 would select frequency band 750 Hz. User interface 505 includes next frequency band selection element 530 that allows the user to move from a currently selected frequency band to a next frequency band in the order of frequency bands. Alternatively, the user can directly select the frequency band by touching the frequency bar corresponding to the frequency band.

User interface 505 includes start/stop tone selection element 550 that allows a user to start and stop a tone corresponding to the currently selected frequency band. For example, if the currently selected frequency band is 250 Hz and there is no tone currently being generated, selection of start/stop tone selection element 550 causes tone generation component 210 to generate a tone corresponding to frequency band 250 Hz which can be heard through headset 140. If there is already a tone being generated, then selection of start/stop tone selection element 550 causes tone generation component 210 to cease generation of the tone corresponding to frequency band 250 Hz.

User interface 505 also includes switch ear selection element 520 that causes a tone being generated for a corresponding frequency band to be output for the opposite ear from which it is currently being output, as well as update the display to display information corresponding to the currently selected ear. For example, if the tone corresponding to frequency band 250 Hz is currently being output for the right ear (e.g. right earpiece of the headset), selection of switch ear selection element 520 would cause the tone to be output for the left ear (e.g. left earpiece of the headset). It is to be appreciated that in an embodiment, the tone is only output for one ear during testing so the user can focus on that ear. However, in an alternative embodiment, the tone can be output for both ears concurrently.

User interface component 505 includes a current selection information box 535 that displays information pertaining to the currently selected ear and frequency band. For example, current selection information box 535 can indicate the currently selected ear, the currently selected frequency band, and/or the currently selected signal level for the currently selected frequency band. However, it is to be appreciated that any suitable information can be displayed in current selection information box 535 pertaining to the user's current selections or results of hearing sensitivity testing. User interface 505 also includes normal hearing curve element 555 that depicts the normal hearing curve for a set of users across the displayed frequency bands.

Hearing sensitivity component 120 also includes sensitivity results component 230 that generates results of hearing sensitivity testing. As a user conducts hearing sensitivity testing, the results of the testing can be stored by sensitivity results component 230. It is to be appreciated that the results can be stored without identifying information for the user or can be stored with identifying information, for example in a user profile. In examples herein, results will be described with identifying information for the user. Hearing sensitivity testing results can include identifying information for the user, and for each ear and frequency band a resulting minimum signal level at which the user was able to hear the corresponding tone for the frequency band. FIG. 6 depicts a non-limiting example of hearing sensitivity testing results records 610, 620, and 630 for USERS 1 to N, where N is an integer representing the number of users for which hearing sensitivity testing results have been recorded, for M frequency bands, where M is an integer representing the number of frequency bands for which hearing sensitivity testing results have been recorded. The hearing sensitivity testing results records 610, 620, and 630 include user name, frequency band left and right ear minimum signal level values where the user was able to the hear the tone corresponding to the frequency band. The minimum signal level values can be relative or absolute in value. The minimum signal level values can directly represent your hearing sensitivity or can be used to generate other parameters or coefficients for filter design, for example, for a hearing aid or hearing assistance device.

In a non-limiting example, a user can employ the selection elements of user interface 505 to select a frequency band (e.g. using previous frequency band selection element 525, next frequency band selection element 530, or touching the frequency bar), select an ear (e.g. using switch ear selection element 520), and start a corresponding tone (e.g. using start/stop tone selection element 550). The user can increase or decrease (e.g. increase signal level selectable element 510 and decrease signal level selectable element 515) the signal level until they can just barely hear the tone, thus identifying the minimum signal level for which this is able to hear the tone corresponding to the frequency band. The user can stop the corresponding tone (e.g. using start/stop tone selection element 550). It is to be appreciated that in an embodiment the start/stop tone selection element 550 is optional. The tone can continually be generated corresponding to the current frequency band selection. The user can perform this test for each ear and frequency band. For example, the user may start at a low signal level and increase the signal level until they can hear the tone, then decrease the signal until they cannot hear the tone, then increase it again until they can hear the tone, then repeat as desired. In this manner, the user will narrow down the signal level for which they can barely hear the tone. It is to be appreciated that tone generation component can change the granularity at which the signal level changes with each selection of the increase signal level selectable element 510 and decrease signal level selectable element 515, for example, at each change in direction of the signal level. For example, during the initial increasing of the signal level, each selection of the increase signal level selectable element 510, can result in an increase of the signal level by first amount, when the user selects the decrease signal level selectable element 515, the signal level can decrease by a second amount that is less than the third amount. This can continue at each change in direction allowing the user to narrow in on the signal level at which they can barely hear the tone using finer grained changes in signal level. It is also to be appreciated that the user can start at a higher signal level and decrease the signal level until they don't hear the tone, and continue as described above until the narrow in on the signal level at which they can barely hear the tone. Generally, the user should be able to identify the signal level at which they can barely hear the tone in three intervals increase-decrease-increase signal level, or decrease-increase-decrease signal level, however, any suitable number of intervals T can be employed.

Sensitivity results component 230 can keep track of the most recent signal level that the user set for the corresponding ear and frequency band in the hearing sensitivity testing results record for the user. It is to be appreciated that sensitivity results component 230 can also keep track of client device 110 and/or headset 140 metadata in the hearing sensitivity testing results record. As such, a user may have multiple hearing sensitivity testing results records respectively corresponding to client devices 110 and/or headsets 140. For example, a user may have respective hearing sensitivity testing results records for a mobile phone, game console, tablet, personal computer, laptop, wired headset, Bluetooth headset, etc.

Sensitivity results component 230 can generate a normal hearing curve for client device 110 and/or headset 140 using hearing sensitivity testing results records stored on client device 110. For example, sensitivity results component 230 can determine an average signal level value for each frequency band and ear from the data recorded in the hearing sensitivity testing results records. Sensitivity testing results component 230 can use the average signal level values to generate the normal hearing curve. In alternative embodiments, sensitivity results component 230 can determine a median signal level value, a mode signal level value, a geometric mean signal value, a harmonic mean signal level value, or a quadratic mean signal level value for each frequency band and ear from the data recorded in the hearing sensitivity testing results records, and employ those values in generating the normal hearing curve.

Figure 8A:
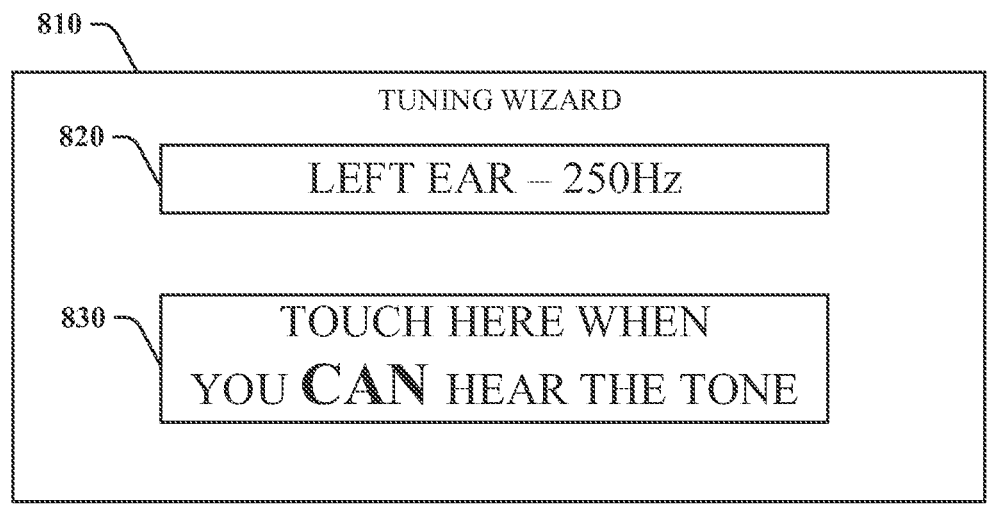
FIG. 8A illustrates a diagram of an exemplary non-limiting user interface for a tuning wizard while increasing signal level on a client device for estimating hearing sensitivity in accordance with an implementation of this disclosure.
Figure 8B:
FIG. 8B illustrates a diagram of an exemplary non-limiting user interface for a tuning wizard while decreasing signal level on a client device for estimating hearing sensitivity in accordance with an implementation of this disclosure.

Hearing sensitivity component 120 also includes sensitivity wizard component 240 that automates many hearing sensitivity testing features described above. FIG. 7 depicts a non-limiting exemplary user interface 710, having many elements similar to user interface 505. User interface 710 includes a tuning wizard selection element 720 that initiates an automated hearing sensitivity testing by sensitivity wizard component 240. Sensitivity wizard component 240 will test the user's hearing sensitivity for frequency bands 1 to M. For example, sensitivity wizard component 240 can generate a tone for frequency band 1 at a predetermined low signal level and present a user interface 810 as depicted in FIG. 8A. User interface 810 includes element 820 that identifies the current ear and frequency band. User interface 810 also includes touch here when you can hear the tone selection element 830 that informs the user to select the element when they can hear the tone. Sensitivity wizard component 240 will increase the signal level at a predetermined amount per time unit until the user selects touch here when you can hear the tone selection element 830. Upon selection of touch here when you can hear the tone selection element 830, sensitivity wizard component 240 will stop increasing the signal level and display user interface 840 as depicted in FIG. 8B. User interface 840 includes element 820 that identifies the current ear and frequency band, as well as, touch here when you can no longer hear the tone selection element 850 that informs the user to select the element when they can no longer hear the tone. Sensitivity wizard component 240 will decrease the signal level by a predetermined amount per time unit until the user selects touch here when you can no longer hear the tone selection element 850. Upon selection of touch here when you can no longer hear the tone selection element 850, sensitivity wizard component 240 will stop decreasing the signal level, display user interface 810. Sensitivity wizard component 240 will alternate between user interface 810 with increasing signal level and user interface 840 with decreasing signal level a predetermined number of intervals T. It is to be appreciated that the predetermined number of intervals can be a user setting, administrator setting, or dynamically determined. After the predetermined number of intervals, sensitivity results component 230 will record the signal level at which the signal level stopped changing in the hearing sensitivity testing results record corresponding to the ear and frequency band. Sensitivity wizard component 240 will then continue to conduct the above hearing sensitivity testing for each frequency band for each ear, and sensitivity results component 230 will record the signal level at which the signal level stopped changing in the hearing sensitivity testing results record corresponding to the ear and frequency band. As described above, sensitivity wizard component 240 can employ changes in granularity of signal level change at each alternation between user interfaces 810 and 840. It is to be appreciated that sensitivity wizard component 240 can begin tuning wizard with user interface 840 and decreasing signal level from a predetermined high signal level.

Figure 9:
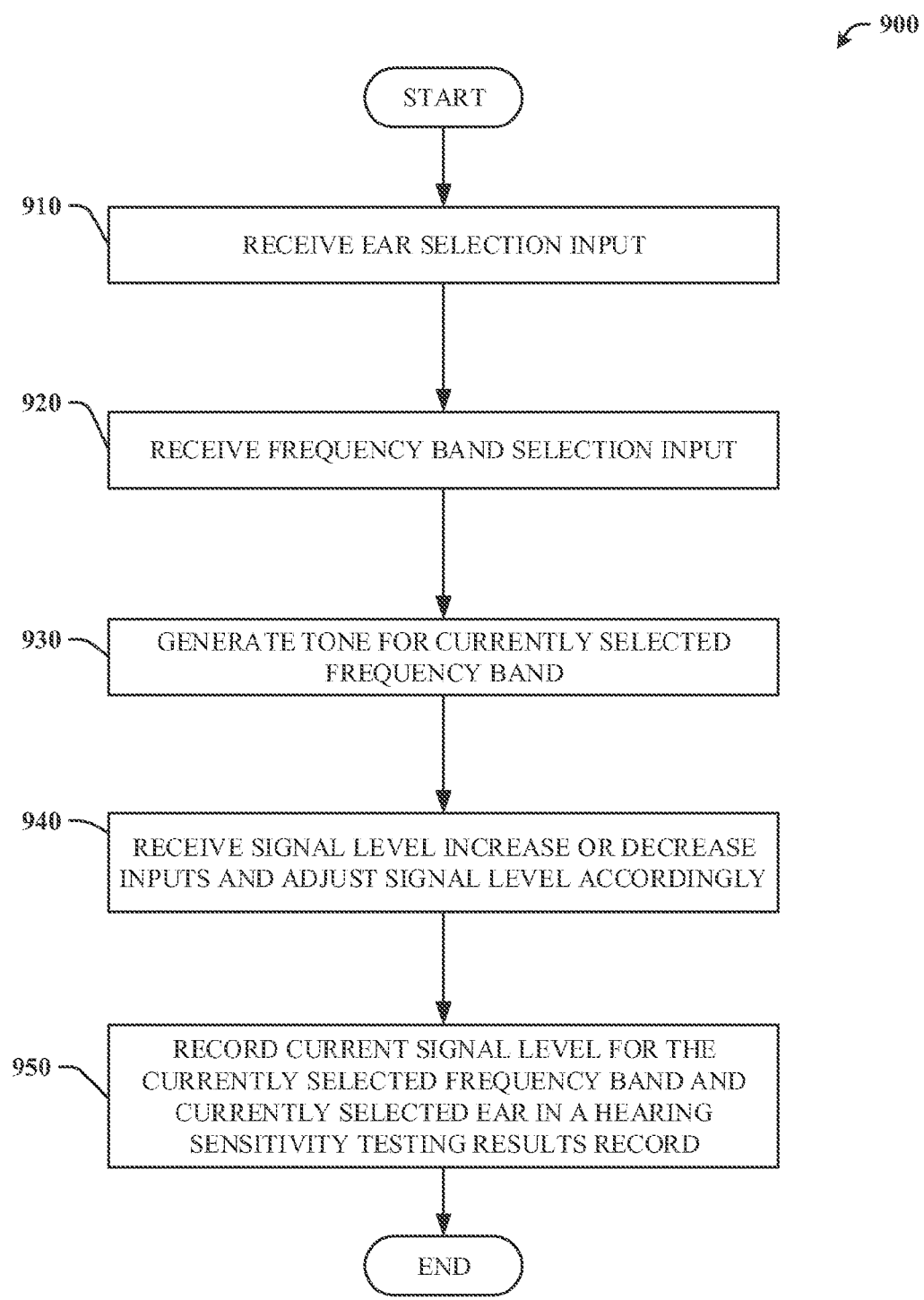
FIG. 9 illustrates an exemplary non-limiting flow diagram for generating hearing sensitivity results for a user in accordance with an implementation of this disclosure.
Figure 10A:
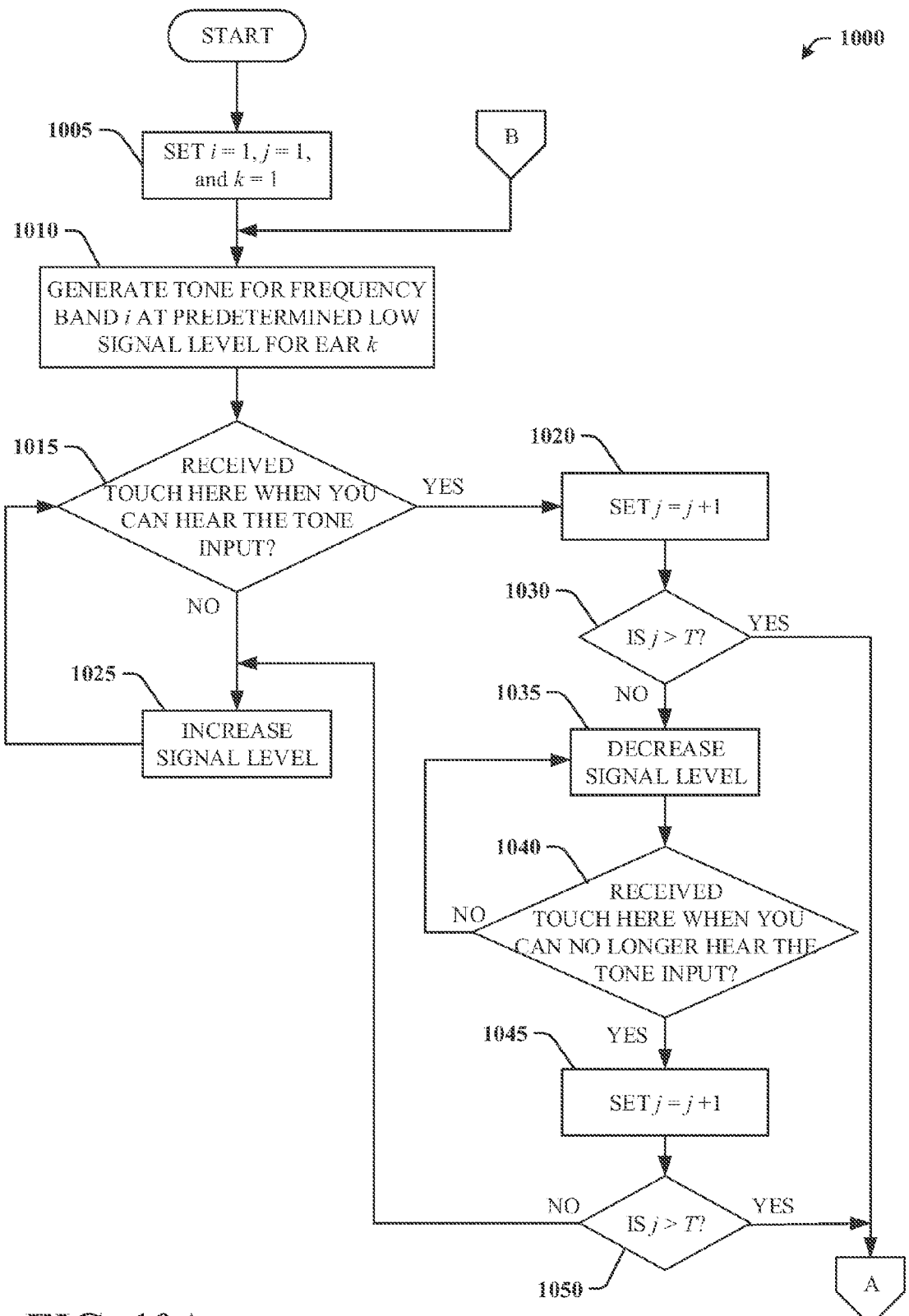
FIGS. 10A and 10B illustrates an exemplary non-limiting flow diagram for generating hearing sensitivity results for a user via tuning wizard in accordance with an implementation of this disclosure.
Figure 10B:
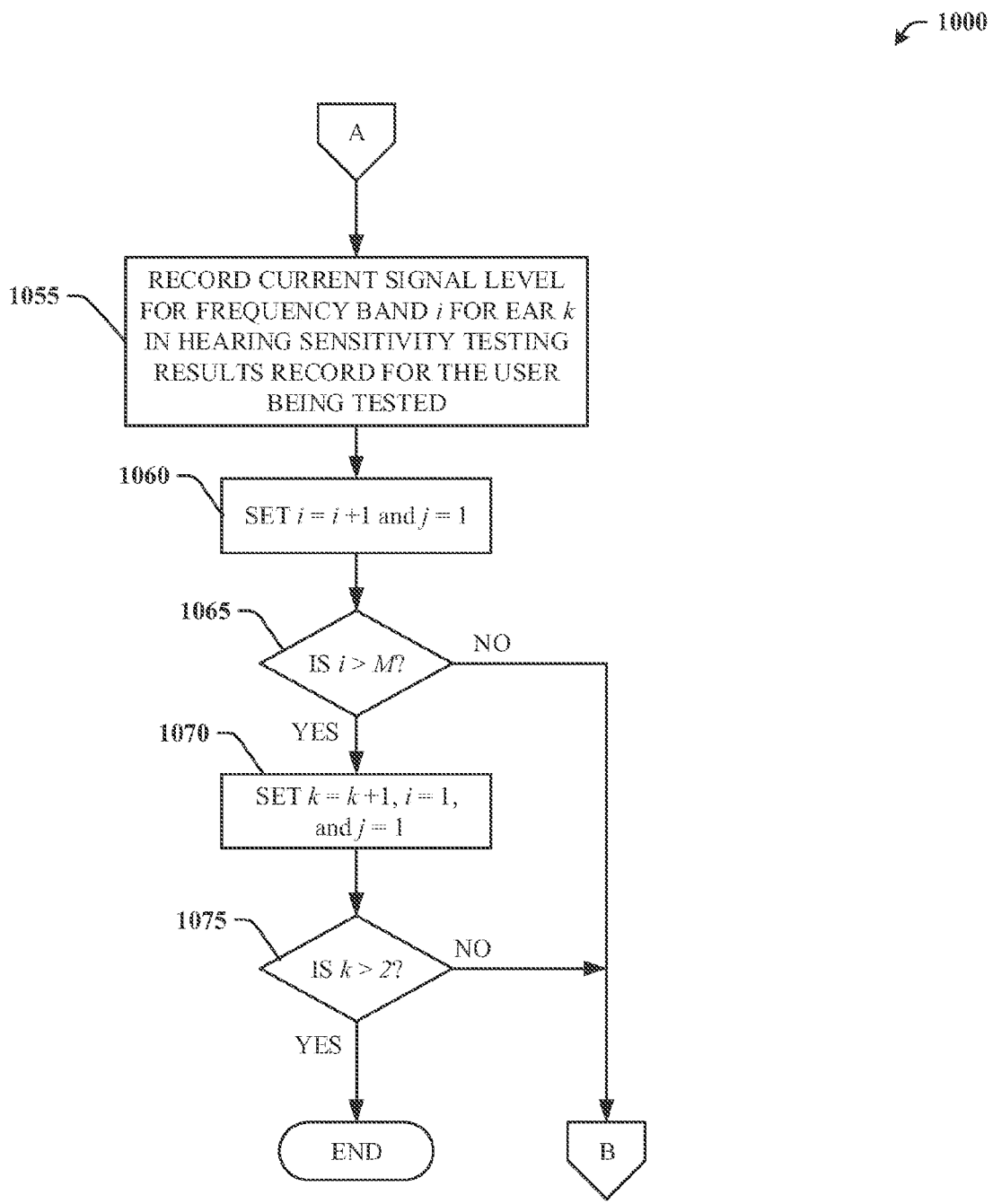

FIGS. 9-10B illustrate various methods in accordance with certain disclosed aspects. While, for purposes of simplicity of explanation, the methodologies are shown and described as a series of acts, it is to be understood and appreciated that the disclosed aspects are not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with certain disclosed aspects. Additionally, it is to be further appreciated that the methodologies disclosed hereinafter and throughout this disclosure are capable of being stored on an article of manufacture to facilitate transporting and transferring such methodologies to computers.

Referring to FIG. 9, an exemplary method 900 for generating hearing sensitivity results for a user is depicted. At reference numeral 910, an ear selection input is received indicating a currently selected ear (e.g., by a user interface component 220, sensitivity results component 230, hearing sensitivity component 120, or client device 110). At reference numeral 920, a frequency band selection input is received indicating a currently selected frequency band (e.g., by a user interface component 220, sensitivity results component 230, hearing sensitivity component 120, or client device 110). At reference numeral 930, a tone corresponding to the currently selected frequency band is outputted for the currently selected ear (e.g., by a tone generation component 210, user interface component 220, hearing sensitivity component 120, or client device 110). At reference numeral 940, one or more signal level increase inputs or signal level decrease inputs are received and the signal level is adjusted to the one or more signal level increase inputs or signal level decrease inputs (e.g., by a tone generation component 210, user interface component 220, hearing sensitivity component 120, or client device 110). At reference numeral 950, a current signal level is recorded for the currently selected frequency band and currently selected ear in a hearing sensitivity testing results record (e.g., by a user interface component 220, sensitivity results component 230, hearing sensitivity component 120, or client device 110).

Referring to FIGS. 10A and 10B, an exemplary method 1000 for generating hearing sensitivity results for a user using a tuning wizard is depicted. At reference numeral 1005, variables i, j, and k, are set to a value of, where i is employed as a counter to track the frequency bands tested up to the number of frequency bands M, j is used as a counter to track the intervals of increasing signal level and decreasing signal level up to the predetermined number of intervals T (e.g. T=3 would correspond to an three intervals—increasing, decreasing, and increasing), and k is employed to track the number of ears up to two ears, left and right. It is to be appreciated that for k, left ear (k=1) can be tested before right ear (k=2), or right ear (k=1) can be tested before left ear (k=2) (e.g., by a sensitivity wizard component 240, user interface component 220, hearing sensitivity component 120, or client device 110). At reference numeral 1010, a tone is outputted for frequency band i for ear k. (e.g., by a sensitivity wizard component 240, user interface component 220, tone generation component 210, hearing sensitivity component 120, or client device 110). At reference numeral 1015, a determination is made whether a touch here when you can hear the tone input is received (e.g., by a sensitivity wizard component 240, user interface component 220, hearing sensitivity component 120, or client device 110). If the determination at 1015 is "NO" meaning that a determination has been made that the touch here when you can hear the tone input has not been received, the method proceeds to element 1025. If the determination at 1015 is "YES" meaning that a determination has been made that the touch here when you can hear the tone input has been received, the method proceeds to element 1020. At reference number 1025, the signal level of the tone is increased by a predetermined amount. At reference number 1020, j is incremented by one. At reference numeral 1030, a determination is made whether j is greater than T (e.g., by a sensitivity wizard component 240, user interface component 220, hearing sensitivity component 120, or client device 110). If the determination at 1030 is "NO" meaning that a determination has been made that j is not greater than T, the method proceeds to element 1035. If the determination at 1030 is "YES" meaning that a determination has been made that j is greater than T, the method proceeds to element 1055. At reference number 1035, the signal level of the tone is decreased by a predetermined amount. At reference numeral 1040, a determination is made whether a touch here when you can no longer hear the tone input is received (e.g., by a sensitivity wizard component 240, user interface component 220, hearing sensitivity component 120, or client device 110). If the determination at 1040 is "NO" meaning that a determination has been made that the touch here when you can no longer hear the tone input has not been received, the method proceeds to element 1035. If the determination at 1040 is "YES" meaning that a determination has been made that the touch here when you can no longer hear the tone input has been received, the method proceeds to element 1045. At reference number 1045, j is incremented by one. At reference numeral 1050, a determination is made whether j is greater than T (e.g., by a sensitivity wizard component 240, user interface component 220, hearing sensitivity component 120, or client device 110). If the determination at 1050 is "NO" meaning that a determination has been made that j is not greater than T, the method proceeds to element 1025. If the determination at 1050 is "YES" meaning that a determination has been made that j is greater than T, the method proceeds to element 1055. At reference numeral 1055, the current signal level for frequency band i for ear k is recorded in a hearing sensitivity testing results record for the current user being tested (e.g., by a sensitivity wizard component 240, user interface component 220, sensitivity results component 230, hearing sensitivity component 120, or client device 110). At reference number 1060, i is incremented by one and j is set to a value of one. (e.g., by a sensitivity wizard component 240, user interface component 220, hearing sensitivity component 120, or client device 110). At reference numeral 1065, a determination is made whether i is greater than M (e.g., by a sensitivity wizard component 240, user interface component 220, hearing sensitivity component 120, or client device 110). If the determination at 1065 is "NO" meaning that a determination has been made that i is not greater than M, the method proceeds to element 1010. If the determination at 1050 is "YES" meaning that a determination has been made that i is greater than M, the method proceeds to element 1070. At reference number 1070, k is incremented by one, and i and j are set to a value of one. (e.g., by a sensitivity wizard component 240, user interface component 220, hearing sensitivity component 120, or client device 110). At reference numeral 1075, a determination is made whether k is greater than 2 (e.g., by a sensitivity wizard component 240, user interface component 220, hearing sensitivity component 120, or client device 110). If the determination at 1075 is "NO" meaning that a determination has been made that k is not greater than 2, the method proceeds to element 1010. If the determination at 1075 is "YES" meaning that a determination has been made that k is greater than 2, the method ends.

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store where media may be found. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various embodiments of this disclosure.

Figure 11:
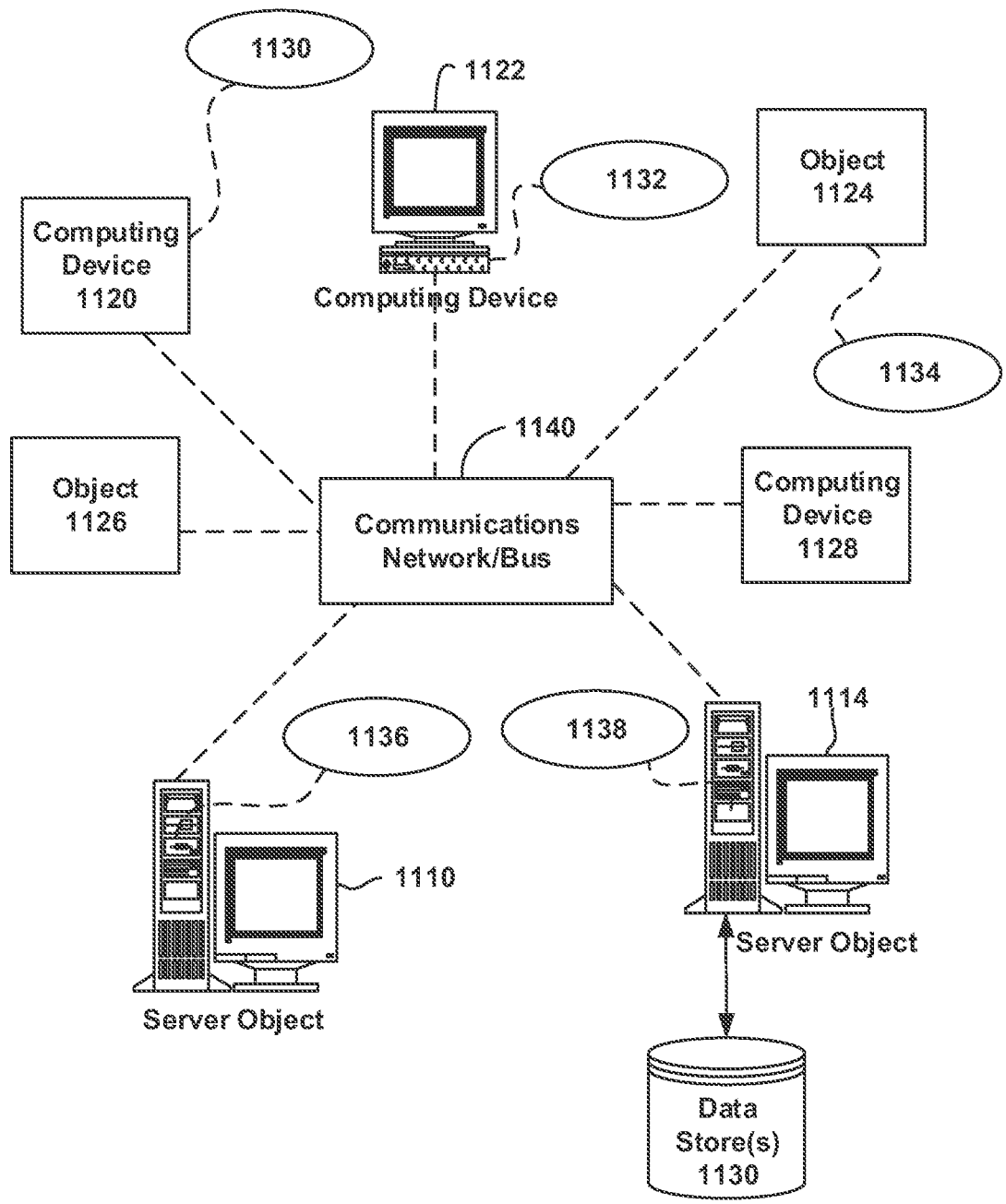
FIG. 11 illustrates a block diagram of an exemplary non-limiting networked environment in which various embodiments can be implemented.

FIG. 11 provides a schematic diagram of an exemplary networked or distributed computing environment. The distributed computing environment comprises computing objects 1110, 1112, etc. and computing objects or devices 1120, 1122, 1124, 1126, 1128, etc., which may include programs, methods, data stores, programmable logic, etc., as represented by applications 1130, 1132, 1134, 1136, 1138. It can be appreciated that computing objects 1110, 1112, etc. and computing objects or devices 1120, 1122, 1124, 1126, 1128, etc. may comprise different devices, such as personal digital assistants (PDAs), audio/video devices, mobile phones, MP3 players, personal computers, laptops, tablets, etc.

Each computing object 1110, 1112, etc. and computing objects or devices 1120, 1122, 1124, 1126, 1128, etc. can communicate with one or more other computing objects 1110, 1112, etc. and computing objects or devices 1120, 1122, 1124, 1126, 1128, etc. by way of the communications network 1140, either directly or indirectly. Even though illustrated as a single element in FIG. 11, network 1140 may comprise other computing objects and computing devices that provide services to the system of FIG. 11, and/or may represent multiple interconnected networks, which are not shown. Each computing object 1110, 1112, etc. or computing objects or devices 1120, 1122, 1124, 1126, 1128, etc. can also contain an application, such as applications 1130, 1132, 1134, 1136, 1138, that might make use of an API, or other object, software, firmware and/or hardware, suitable for communication with or implementation of various embodiments of this disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any suitable network infrastructure can be used for exemplary communications made incident to the systems as described in various embodiments herein.

Thus, a host of network topologies and network infrastructures, such as client/server, peer-to-peer, or hybrid architectures, can be utilized. The "client" is a member of a class or group that uses the services of another class or group. A client can be a computer process, e.g., roughly a set of instructions or tasks, that requests a service provided by another program or process. A client process may utilize the requested service without having to "know" all working details about the other program or the service itself.

In a client/server architecture, particularly a networked system, a client can be a computer that accesses shared network resources provided by another computer, e.g., a server. In the illustration of FIG. 11, as a non-limiting example, computing objects or devices 1120, 1122, 1124, 1126, 1128, etc. can be thought of as clients and computing objects 1110, 1112, etc. can be thought of as servers where computing objects 1110, 1112, etc. provide data services, such as receiving data from client computing objects or devices 1120, 1122, 1124, 1126, 1128, etc., storing of data, processing of data, transmitting data to client computing objects or devices 1120, 1122, 1124, 1126, 1128, etc., although any computer can be considered a client, a server, or both, depending on the circumstances. Any of these computing devices may be processing data, or requesting transaction services or tasks that may implicate the techniques for systems as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the techniques described herein can be provided standalone, or distributed across multiple computing devices or objects.

In a network environment in which the communications network/bus 1140 is the Internet, for example, the computing objects 1110, 1112, etc. can be Web servers, file servers, media servers, etc. with which the client computing objects or devices 1120, 1122, 1124, 1126, 1128, etc. communicate via any of a number of known protocols, such as the hypertext transfer protocol (HTTP). Objects 1110, 1112, etc. may also serve as client computing objects or devices 1120, 1122, 1124, 1126, 1128, etc., as may be characteristic of a distributed computing environment.

Exemplary Computing Device

Figure 12:
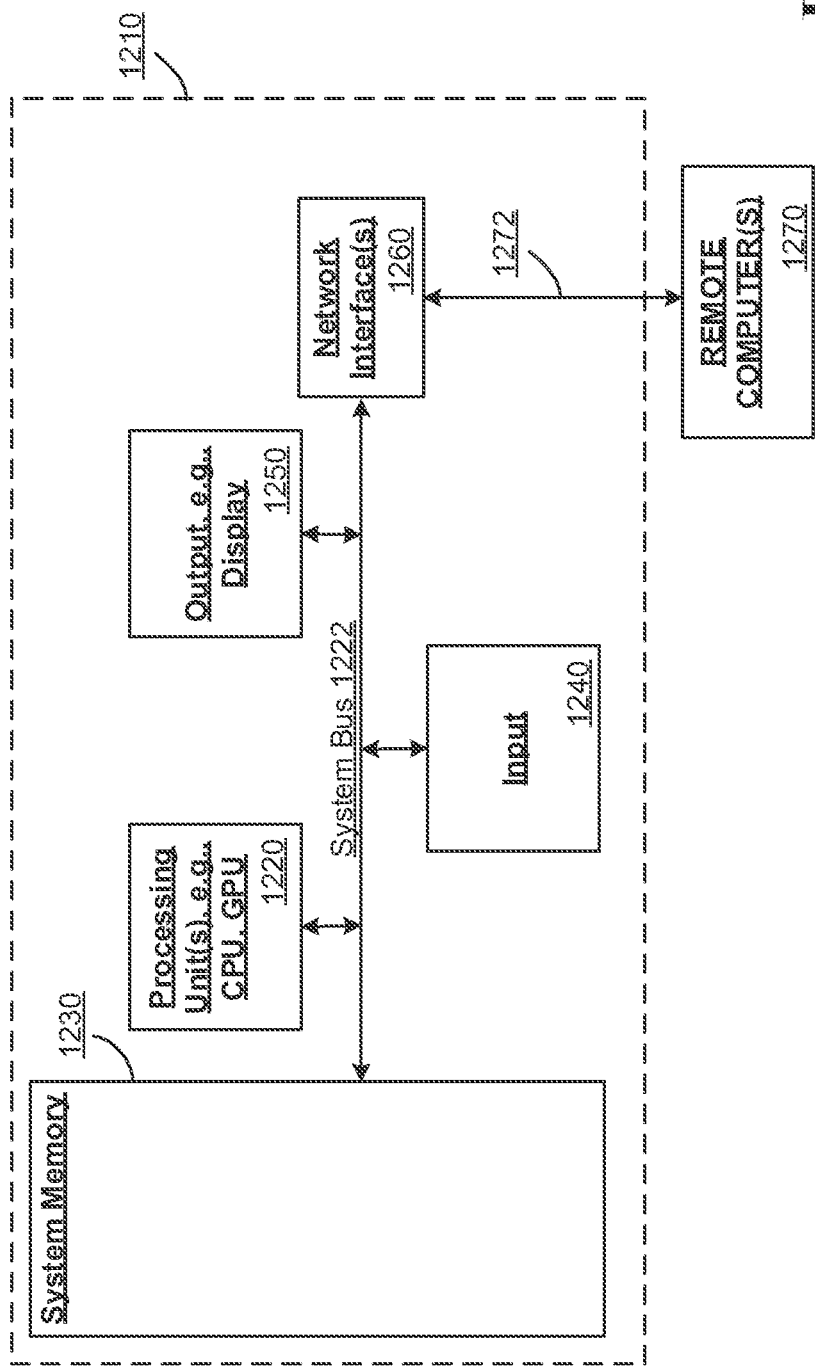
FIG. 12 illustrates a block diagram of an exemplary non-limiting computing system or operating environment in which various embodiments can be implemented.

As mentioned, advantageously, the techniques described herein can be applied to any suitable device. It is to be understood, therefore, that handheld, portable and other computing devices and computing objects of all kinds are contemplated for use in connection with the various embodiments. Accordingly, the computer described below in FIG. 12 is but one example of a computing device that can be employed with implementing one or more of the systems or methods shown and described in connection with FIGS. 1-10A. Additionally, a suitable server can include one or more aspects of the below computer, such as a media server or other media management server components.

Although not required, embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 12 thus illustrates an example of a suitable computing system environment 1200 in which one or aspects of the embodiments described herein can be implemented, although as made clear above, the computing system environment 1200 is only one example of a suitable computing environment and is not intended to suggest any limitation as to scope of use or functionality. Neither is the computing environment 1200 be interpreted as having any dependency or requirement relating to any one or combination of components illustrated in the exemplary operating environment 1200.

With reference to FIG. 12, an exemplary computing device for implementing one or more embodiments in the form of a computer 1210 is depicted. Components of computer 1210 may include, but are not limited to, a processing unit 1220, a system memory 1230, and a system bus 1222 that couples various system components including the system memory to the processing unit 1220.

Computer 1210 typically includes a variety of computer readable media and can be any available media that can be accessed by computer 1210. The system memory 1230 may include computer storage media in the form of volatile and/or nonvolatile memory such as read only memory (ROM) and/or random access memory (RAM). By way of example, and not limitation, system memory 1230 may also include an operating system, application programs, other program modules, and program data.

A user can enter commands and information into the computer 1210 through input devices 1240, non-limiting examples of which can include a keyboard, keypad, a pointing device, a mouse, stylus, touchpad, touchscreen, trackball, motion detector, camera, microphone, joystick, game pad, scanner, or any other device that allows the user to interact with computer 1210. A monitor or other type of display device is also connected to the system bus 1222 via an interface, such as output interface 1250. In addition to a monitor, computers can also include other peripheral output devices such as speakers and a printer, which may be connected through output interface 1250.

The computer 1210 may operate in a networked or distributed environment using logical connections to one or more other remote computers, such as remote computer 1270. The remote computer 1270 may be a personal computer, a server, a router, a network PC, a peer device or other common network node, or any other remote media consumption or transmission device, and may include any or all of the elements described above relative to the computer 1210. The logical connections depicted in FIG. 12 include a network 1272, such local area network (LAN) or a wide area network (WAN), but may also include other networks/buses e.g., cellular networks.

As mentioned above, while exemplary embodiments have been described in connection with various computing devices and network architectures, the underlying concepts may be applied to any network system and any computing device or system in which it is desirable to publish or consume media in a flexible way.

Also, there are multiple ways to implement the same or similar functionality, e.g., an appropriate API, tool kit, driver code, operating system, control, standalone or downloadable software object, etc. which enables applications and services to take advantage of the techniques described herein. Thus, embodiments herein are contemplated from the standpoint of an API (or other software object), as well as from a software or hardware object that implements one or more aspects described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the aspects disclosed herein are not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function (e.g., coding and/or decoding); software stored on a computer readable medium; or a combination thereof.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In order to provide for or aid in the numerous inferences described herein (e.g. inferring relationships between metadata or inferring topics of interest to users), components described herein can examine the entirety or a subset of the data to which it is granted access and can provide for reasoning about or infer states of the system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

In view of the exemplary systems described above, methodologies that may be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention is not to be limited to any single embodiment, but rather can be construed in breadth, spirit and scope in accordance with the appended claims.

What is claimed is:

1. A method, comprising: outputting, by a device including a processor, a tone corresponding to a currently selected frequency band to a currently selected ear at a signal level of a first predetermined value; adjusting, by the device, the signal level of the outputted tone in a first direction at a granularity level until receiving a first input, wherein the first direction is one of increasing or decreasing, wherein the first input indicates hearing of the outputted tone by a user if the first direction is increasing or the first input indicates not hearing of the outputted tone by the user if the first direction is decreasing, and receiving, by the device, the first inputs adjusting, by the device, the signal level of the outputted tone in a second direction at a finer granularity level than the granularity level in the first direction until receiving a second input, wherein the second direction is opposite the first direction, wherein the second input indicates hearing of the outputted tone by the user if the second direction is increasing or the second input indicates not hearing of the outputted tone by the user if the second direction is decreasing, and receiving, by the device, the second input; repeating, by the device, at least one of the adjusting the signal level of the outputted tone in the first direction and the receiving the first input or the adjusting the signal level of the outputted tone in the second direction and the receiving the second input until a predetermined number of changes in direction has occurred, wherein at each change in direction the granularity level is made finer than an immediately preceding direction; and recording, by the device, a current signal level of the outputted tone for the currently selected frequency band and the currently selected ear in a hearing sensitivity testing results record.

2. The method of claim 1, further comprising receiving, by the device, a frequency band selection input indicating selection of the currently selected frequency band.

3. The method of claim 1, further comprising receiving, by the device, an ear selection input indicating selection of the currently selected ear.

4. The method of claim 1, wherein the predetermined number of changes in direction is greater than three.

5. The method of claim 1, further comprising: receiving, by the device, another frequency band selection input indicating selection of the another frequency band; outputting, by the device, another tone corresponding to the other frequency band to the currently selected ear at another signal level of a second predetermined value; adjusting, by the device, the other signal level of the outputted other tone in the first direction at the granularity level until receiving the first input, and receiving, by the device, the first inputs; adjusting, by the device, the other signal level of the outputted other tone in the second direction at the finer granularity level than the granularity level in the first direction until receiving the second input, and receiving, by the device, the second input; repeating, by the device at least one of the adjusting the other signal level of the outputted other tone in the first direction and the receiving the first input or the adjusting the other signal level of the outputted other tone in the second direction and the receiving the second input until the predetermined number of changes in direction has occurred, wherein at each change in direction the granularity level is made finer than the immediately preceding direction: and recording, by the device, another current signal level of the outputted other tone for the other selected frequency band and the currently selected ear in the hearing sensitivity testing results record.

6. The method of claim 1, further comprising: receiving, by the device, another ear selection input indicating selection of another ear; outputting, by the device, the tone corresponding to the currently selected frequency band to the other ear at the signal level of the first predetermined value; adjusting, by the device, the signal level of the outputted tone in the first direction at the granularity level until receiving the first input, and receiving, by the device, the first inputs; adjusting, by the device, the signal level of the outputted tone in the second direction at the finer granularity level than the granularity level in the first direction until receiving the second input, and receiving, by the device, the second input; repeating, by the device at least one of the adjusting the signal level of the outputted tone in the first direction and the receiving the first input or the adjusting the signal level of the outputted tone in the second direction and the receiving the second input until the predetermined number of changes in direction has occurred, wherein at each change in direction the granularity level is made finer than the immediately preceding direction: and recording, by the device, another current signal level of the outputted tone for the currently selected frequency band and the other ear in the hearing sensitivity testing results record.

7. The method of claim 1, further comprising: adding, by the device, metadata to the hearing sensitivity testing results record comprising at least one of an attribute of a user associated with the hearing sensitivity testing results record, an attribute of a client device associated with the hearing sensitivity testing results record, or an attribute of a headset associated with the hearing sensitivity testing results record.

8. A non-transitory computer-readable medium having instructions stored thereon that, in response to execution, cause a system including a processor to perform operations comprising: outputting a tone corresponding to a currently selected frequency band to a currently selected ear at a signal level of a first predetermined value; adjusting the signal level of the outputted tone in a first direction at a granularity level until receiving a first input, wherein the first direction is one of increasing or decreasing, wherein the first input indicates hearing of the outputted tone by a user if the first direction is increasing or the first input indicates not hearing of the outputted tone by the user if the first direction is decreasing, and receiving the first inputs; adjusting the signal level of the outputted tone in a second direction at a finer granularity level than the granularity level in the first direction until receiving a second input, wherein the second direction is opposite the first direction, wherein the second input indicates hearing of the outputted tone by the user if the second direction is increasing or the second input indicates not hearing of the outputted tone by the user if the second direction is decreasing, and receiving, by the device, the second input; repeating at least one of the adjusting the signal level of the outputted tone in the first direction and the receiving the first input or the adjusting the signal level of the outputted tone in the second direction and the receiving the second input until a predetermined number of changes in direction has occurred, wherein at each change in direction the granularity level is made finer than an immediately preceding direction: and recording a current signal level of the outputted tone for the currently selected frequency band and the currently selected ear in a hearing sensitivity testing results record.

9. The non-transitory computer-readable medium of claim 8, the operations further comprising receiving a frequency band selection input indicating selection of the currently selected frequency band.

10. The non-transitory computer-readable medium of claim 8, the operations further comprising receiving an ear selection input indicating selection of the currently selected ear.

11. The non-transitory computer-readable medium of claim 8, wherein the predetermined number of changes in direction is greater than three.

12. The non-transitory computer-readable medium of claim 8, the operations further comprising: receiving another frequency band selection input indicating selection of the another frequency band; outputting another tone corresponding to the other frequency band to the currently selected ear at another signal level of a second predetermined value; adjusting the other signal level of the outputted other tone in the first direction at the granularity level until receiving the first input, and receiving the first inputs; adjusting the other signal level of the outputted other tone in the second direction at the finer granularity level than the granularity level in the first direction until receiving the second input, and receiving the second input: repeating at least one of the adjusting the other signal level of the outputted other tone in the first direction and the receiving the first input or the adjusting the other signal level of the outputted other tone in the second direction and the receiving the second input until the predetermined number of changes in direction has occurred, wherein at each change in direction the granularity level is made finer than the immediately preceding direction: and recording another current signal level of the outputted other tone for the other selected frequency band and the currently selected ear in the hearing sensitivity testing results record.

13. The non-transitory computer-readable medium of claim 8, the operations further comprising: receiving another ear selection input indicating selection of another ear; outputting the tone corresponding to the currently selected frequency band to the other ear at the signal level of the first predetermined value; adjusting the signal level of the outputted tone in the first direction at the granularity level until receiving the first input, and receiving the first inputs; adjusting the signal level of the outputted tone in the second direction at the finer granularity level than the granularity level in the first direction until receiving the second input, and receiving the second input; repeating at least one of the adjusting the signal level of the outputted tone in the first direction and the receiving the first input or the adjusting the signal level of the outputted tone in the second direction and the receiving the second input until the predetermined number of changes in direction has occurred, wherein at each change in direction the granularity level is made finer than the immediately preceding direction: and recording another current signal level of the outputted tone for the currently selected frequency band and the other ear in the hearing sensitivity testing results record.

14. The non-transitory computer-readable medium of claim 8, the operations further comprising: adding metadata to the hearing sensitivity testing results record comprising at least one of attributes of a user associated with the hearing sensitivity testing results record, attributes of a client device associated with the hearing sensitivity testing results record, or attributes of a headset associated with the hearing sensitivity testing results record.

* * * * *